(12) United States Patent
Le Bescond de Coatpont et al.

(10) Patent No.: US 10,289,666 B2
(45) Date of Patent: May 14, 2019

(54) SYSTEM, METHOD AND COMPUTER PROGRAM PRODUCT FOR EDITING WEB PAGES IN-CONTEXT OF A PRODUCTION VIEW

(71) Applicant: Open Text SA ULC, Halifax (CA)

(72) Inventors: Bertrand G. Le Bescond de Coatpont, Austin, TX (US); Ruhul Alam, Austin, TX (US); Mario L. Garcia, Austin, TX (US)

(73) Assignee: Open Text SA ULC, Halifax, CA (US)

( * ) Notice: Subject to any disclaimer, the term of this patent is extended or adjusted under 35 U.S.C. 154(b) by 0 days.

(21) Appl. No.: 15/849,252

(22) Filed: Dec. 20, 2017

(65) Prior Publication Data

US 2018/0113846 A1 Apr. 26, 2018

Related U.S. Application Data

(63) Continuation of application No. 14/029,545, filed on Sep. 17, 2013, now Pat. No. 9,922,013, which is a continuation of application No. 13/280,951, filed on Oct. 25, 2011, now Pat. No. 8,566,704.

(60) Provisional application No. 61/406,475, filed on Oct. 25, 2010.

(51) Int. Cl.
*G06F 17/24* (2006.01)
*G06F 17/22* (2006.01)

(52) U.S. Cl.
CPC .......... *G06F 17/24* (2013.01); *G06F 17/2247* (2013.01)

(58) Field of Classification Search
CPC ..................................................... G06F 17/24
See application file for complete search history.

(56) References Cited

U.S. PATENT DOCUMENTS

| 6,697,825 | B1 | 2/2004 | Underwood et al. |
| 7,500,183 | B2 * | 3/2009 | Kelly ...................... G60F 17/00 |
| 7,802,182 | B2 | 9/2010 | Bales |
| 8,566,704 | B1 | 10/2013 | Le Bescond de Coatpont |
| 9,922,013 | B2 | 3/2018 | Le Bescond de Coatpont et al. |
| 2002/0069204 | A1 | 6/2002 | Kahn et al. |
| 2008/0178122 | A1 | 7/2008 | Becksecker |

(Continued)

OTHER PUBLICATIONS

Office Action for U.S. Appl. No. 13/280,951, dated Dec. 4, 2012, 22 pgs.

(Continued)

*Primary Examiner* — James J Debrow
(74) *Attorney, Agent, or Firm* — Sprinkle IP Law Group

(57) ABSTRACT

Systems and methods for in-context editing of web pages in which the production format of a web page is visible while the web page is being edited, and the editable image is not distorted by the editing tools. In one embodiment, a system includes a server computer, a client computer and a transmission channel coupled between them. The server computer receives a request for a web page from the client computer and responsively transmits a web page containing in-context editing tools to the client computer. The client computer operate alternately in a first mode in which the in-context editing tools are superimposed on a web page image, or a second mode in which the web page image is displayed, but the in-context editing tools are hidden. The tools overlay in the first mode does not alter the production format of the web page image as displayed in the second mode.

21 Claims, 3 Drawing Sheets

(56) References Cited

U.S. PATENT DOCUMENTS

| | | |
|---|---|---|
| 2008/0209311 A1 | 8/2008 | Agronik et al. |
| 2010/0251128 A1 | 9/2010 | Cordasco |
| 2011/0225525 A1* | 9/2011 | Chasman et al. |
| 2012/0151329 A1 | 6/2012 | Cordasco |
| 2014/0019848 A1 | 1/2014 | Le Bescond de Coatpont |

OTHER PUBLICATIONS

Office Action for U.S. Appl. No. 14/029,545, dated Apr. 20, 2016, 12 pgs.
Office Action for U.S. Appl. No. 14/029,545, dated Nov. 1, 2016, 14 pgs.
Office Action for U.S. Appl. No. 14/029,545, dated May 15, 2017, 15 pgs.
Notice of Allowance for U.S. Appl. No. 14/029,545, dated Sep. 21, 2017, 5 pgs.

* cited by examiner

SYSTEM, METHOD AND COMPUTER PROGRAM PRODUCT FOR EDITING WEB PAGES IN-CONTEXT OF A PRODUCTION VIEW

CROSS-REFERENCE TO RELATED APPLICATIONS

This application is a continuation of, and claims a benefit of priority under 35 U.S.C. 120 of the filing date of U.S. patent application Ser. No. 14/029,545 filed Sep. 17, 2013, entitled "System, Method and Computer Program Product for Editing Web Pages In-Context of a Production View," which is a continuation of, and claims a benefit of priority under 35 U.S.C. 120 of the filing date of U.S. patent application Ser. No. 13/280,951 filed Oct. 25, 2011, entitled "System, Method and Computer Program Product for Editing Web Pages In-Context of a Production View," issued as U.S. Pat. No. 8,566,704, which in turn claims the benefit of priority of U.S. Provisional Patent Application No. 61/406,475 filed Oct. 25, 2010, entitled "System and Method for Editing Web Pages In-Context of a Production View," which are all incorporated herein by reference as if set forth herein in their entirety.

TECHNICAL FIELD

This disclosure relates generally to systems and methods for web page editing, and more particularly to systems and methods for in-context editing of web pages so that the production format of the web page is visible while the web page is being edited, and is not altered by the available editing tools.

BACKGROUND

Many companies have large websites that require management of 100,000s and even millions of content items (web pages, images, documents or other content items). Traditionally, editing a web involved displaying the web site in a special preview window that altered how the web page looked when compared to how the web page would look to an external browser. For example, the preview window would include sections of text such as "edit text in this box" between text boxes. Because the instructions "edit text in this box" does not appear in the final web page (e.g., as seen by a site visitor), the user editing the web page had a distorted view of what the web site looked like. In order to see what the web site really looked like, the user would have to open the page with a browser or enter a separate viewing mode. This made managing edits cumbersome.

While some systems allowed the content of the web page to be viewed while the web page was being edited, these systems typically inserted editing tools between the content components. This caused the positions of the components and other aspects of the web page format to change in comparison to the actual production format of the web page. In order to view the production format of the web page, a preview option was provided in which the editing tools were removed to allow the web page components to be viewed in the final production format. Having to switch between the editing and preview environments, however, was inefficient and unwieldy.

SUMMARY

Embodiments disclosed herein provide systems, methods, and computer program products for in-context editing of web pages in which the production format of a web page is visible while the web page is being edited, and the editable image is not distorted by the editing tools. In one particular embodiment, a system for in-context editing of web pages includes a server computer, a client computer and an interconnect coupled between them. The server computer is configured to receive from the client computer a request for a web page, and to transmit a web page to the client computer in response to the request, where the web page contains in-context editing tools. The client computer is configured to operate alternately in one of two modes. In the first mode, the client computer displays the in-context editing tools superimposed on a web page image. In the second mode, the client computer displays the web page image but hides the in-context editing tools. The overlay of the editing tools in the first mode does not alter the production format of the web page image as displayed in the second mode. The server computer may generate the web page using a template that contains the in-context editing tools. The template may be stored in a repository device coupled to the server computer. The in-context editing tools may be developed using Javascript, CSS and HTML elements that reside in a namespace that is unique from a namespace in which components of the web page reside so that they do not present any conflict with the web page components. The system may maintain edited components of the web page in a preview environment until the edited components are published, and may maintain the edited components in a production environment after the edited components are published.

Another embodiment comprises an apparatus. The apparatus includes a computer which is configured to receive a web page template and one or more web page components, and to generate a web page image based upon the template and web page components. The web page image appears in a production format. The computer generates an overlay of one or more editing tools and displays an editable image to a user in an editing environment, where the editable image has the overlay of the editing tools superimposed on the web page image. The overlay of the editing tools does not alter the production format of the web page image. The computer may be configured to update the web page image according to edits entered by a user on the computer, where the updated web page image displayed with the overlay of the editing tools is identical to a production format of the updated web page image.

The overlay of the editing tools may include various tool icons, each of which may be associated with editing tools that are configured to operate only on the component or region with which the tool icon is associated. A visual indicator may be associated with each tool icon to demarcate the corresponding component or region of the web page image with which the tool icon is associated. The tool icons may superimposed on a portion of the corresponding component or region with which they are associated. When a user selects one of the tool icons, the computer may display a corresponding drop down list of user-selectable actions associated with the tool icon that perform corresponding actions on the component or region with which the tool icon is associated. The overlay of editing tools may also include a floating tool palette which has editing tools that can operate on any editable component or region of the web page image. The computer may be configured to alternately enable and disable the editing tools so that when they are enabled, the overlay of tools is superimposed on the web page image, and when the tools are disabled, the overlay is not displayed on the web page image. In either case, the web page image is displayed in the identical production format. The editing tools may include, for instance, Javascript, CSS and HTML elements that reside in a unique namespace from that of components of the web page. The editing tools can then be enabled by enabling all elements in the unique namespace. The computer can be configured to maintain edited components of the web page in a preview environment until the edited components are published, and then maintain the components in a production environment after they are published.

Another alternative embodiment is a software program product. The software program product comprises a non-transitory computer-readable medium which stores one or more program instructions. These instructions are executable by the computer to perform the method that includes receiving a web page template and web page components, generating a production-format web page image based upon the received template and components, generating an overlay of editing tools, and displaying an editable image to a user in an editing environment. The editable image comprises the overlay of the editing tools superimposed on the web page image. The overlay of the editing tools does not alter the production format of the web page image. The method performed by the software product may include selectively enabling or disabling the in-context editing tools. When the in-context editing tools are enabled, an icon for each of the in-context editing tools is superimposed on a portion of a corresponding component or region of the web page image with which the in-context editing tool is associated. Enabling or disabling the in-context editing tools does not alter the format of the web page image. The template may contain the in-context editing tools. Enabling or disabling the in-context editing tools may comprise enabling or disabling all template elements included in a unique namespace associated with the in-context editing tools. The method performed by the software product may include generating, for each of the in-context editing tools, an associated visual indicator that demarcates the corresponding component or region of the web page image with which each in-context editing tool is associated. These visual indicators are superimposed on the boundaries of the corresponding component or region of the web page image. The method performed by the software product may include maintaining edited components of the web page in a preview environment until the edited components are published and, after the edited components are published, maintaining the edited components in a production environment.

Numerous other alternative embodiments are also possible.

BRIEF DESCRIPTION OF THE DRAWINGS

A more complete understanding of the disclosure and the advantages thereof may be acquired by referring to the following description, taken in conjunction with the accompanying drawings in which like reference numbers indicate like features and wherein.

Figure 1:
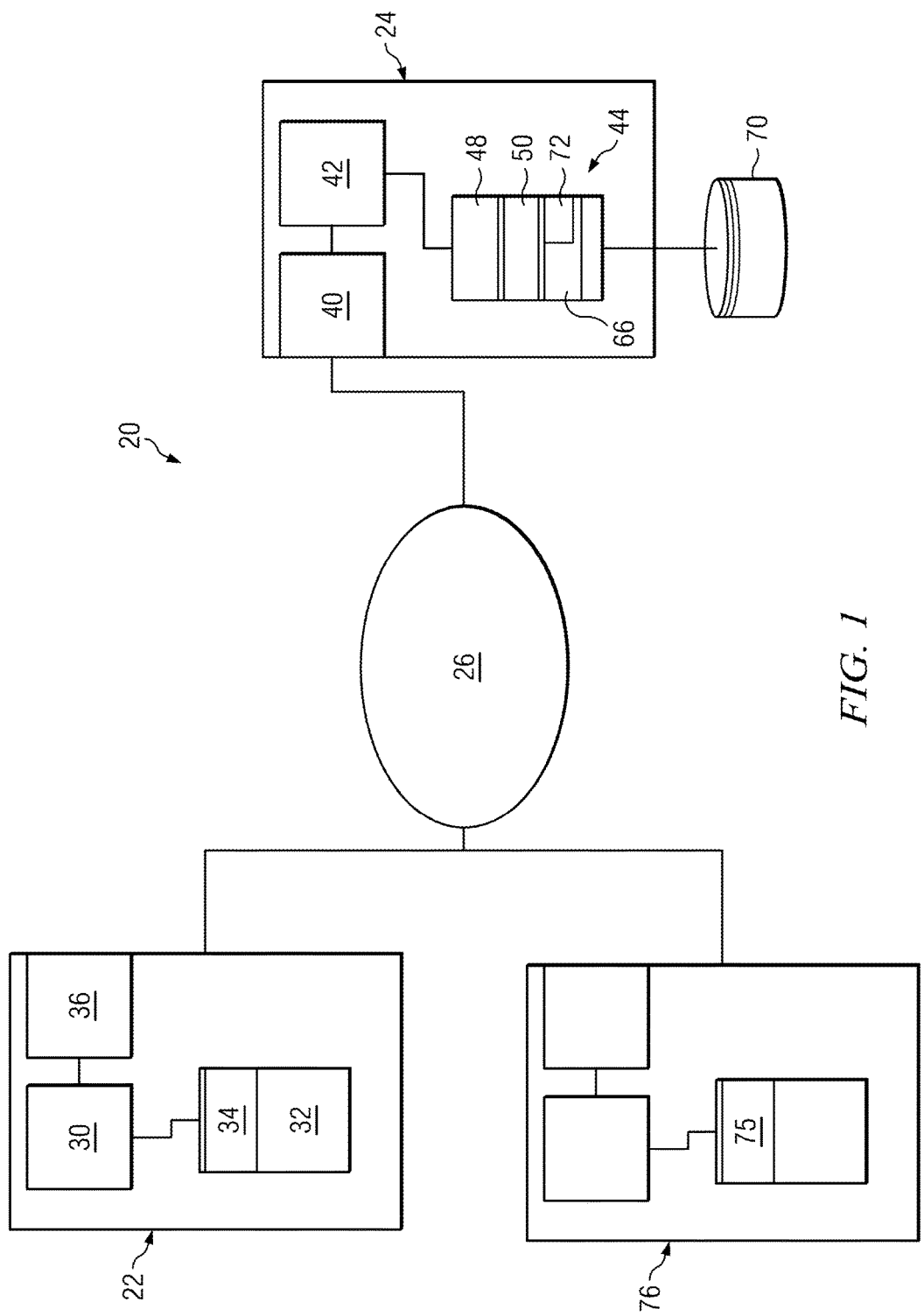
FIG. 1 is a diagram illustrating a simplified client-server computer system in accordance with one embodiment.

The drawings accompanying and forming part of this specification are included to depict certain aspects of the disclosure. It should be noted that the features illustrated in the drawings are not necessarily drawn to scale.

DETAILED DESCRIPTION OF EXEMPLARY EMBODIMENTS

The disclosure and various features and advantageous details thereof are explained more fully with reference to the exemplary, and therefore non-limiting, embodiments illustrated in the accompanying drawings and detailed in the following description. Descriptions of known programming techniques, computer software, hardware, operating platforms and protocols may be omitted so as not to unnecessarily obscure the disclosure in detail. It should be understood, however, that the detailed description and the specific examples, while indicating the preferred embodiments, are given by way of illustration only and not by way of limitation. Various substitutions, modifications, additions and/or rearrangements within the spirit and/or scope of the underlying inventive concept will become apparent to those skilled in the art from this disclosure.

Software implementing embodiments disclosed herein may be implemented in suitable computer-executable instructions that may reside on a computer-readable storage medium. Within this disclosure, the term "computer-readable storage medium" encompasses all types of data storage medium that can be read by a processor. Examples of computer-readable storage media can include random access memories, read-only memories, hard drives, data cartridges, magnetic tapes, floppy diskettes, flash memory drives, optical data storage devices, compact-disc read-only memories, and other appropriate computer memories and data storage devices.

As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited only those elements but may include other elements not expressly listed or inherent to such process, product, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of, any term or terms with which they are utilized. Instead these examples or illustrations are to be regarded as being described with respect to one particular embodiment and as illustrative only. Those of ordinary skill in the art will appreciate that any term or terms with which these examples or illustrations are utilized encompass other embodiments as well as implementations and adaptations thereof which may or may not be given therewith or elsewhere in the specification and all such embodiments are intended to be included within the scope of that term or terms. Language designating such non-limiting examples and illustrations includes, but is not limited to: "for example," "for instance," "e.g.," "in one embodiment," and the like.

Embodiments described herein provide an intuitive system for editing web pages that overlays tools on a production view of the web page to allow the user to preview changes to the production view as edits to the production view are made. Thus, the user can edit the content of the web page as it would appear in its production format.

FIG. 1 illustrates a simplified client-server computer system 20. System 20 includes client computers 22 and 76 and computer 24. Client computers 22, 76 and server computer 24 are connected by a transmission channel 26, which may be a network including a LAN, WAN, the internet or other network.

Client computer 22 can be a standard computer including a central processing unit ("CPU") 30 connected to a computer readable medium 32 (primary and/or secondary). Computer readable medium 32 can comprise any combination of RAM, ROM and/or a magnetic storage device such as a hard drive or other non-transitory computer readable storage medium. Computer readable medium 32 stores a number of computer programs, including a "browser" 34, as known to those in the art. Browser 34 can be used to communicate with remote server computers 24 and to visually present the information received from server computers 24. Client computer 22 establishes network communications through a standard network connection device 36.

Server computer 24 can include standard server computer components, including a network connection device 40, a CPU 42, and a non-transitory computer readable medium 44 (primary and/or secondary memory, disk drives or other non-transitory computer readable media). As shown in FIG. 1, server computer 24 stores a web server program 48 and a page generator program 50 to generate and return web pages in response to requests from server program 48. Server computer 24 can also act as a content management system running content management system program 66 (CMS 66) that manages objects and used to generate web pages. Content and related information can be stored in repository 70. CMS 66 and repository 70 can be used to create, test, modify, manage and store page templates and other content that can be made available to page generator program 50.

According to one embodiment, CMS 66 manages content for web sites as a collection of objects. The collection of objects in a site includes file assets and non-file assets. Non-file assets include assets such as users, groups, modules, module types, pages, menus, themes, structures, styles and templates, logon permissions, administrative permissions, site branding, site content, site navigation, instantiated programming language objects, permissions, user preferences and settings. Various content objects may reference file assets including resources such as code including JSP pages, ASP pages, Java classes and/or object oriented programming language classes, and images including GIF files, etc.

Content items can be stored as corresponding content objects in a repository 70. In some cases, rather than storing the content items, repository 70 can include references to another system and its corresponding objects or repository). Each content object can have an arbitrary amount of metadata associated with it. For purposes of managing a web site, such metadata may include whether the content object has been approved for publication, whether it was published, or any other information that is useful in classifying the content object for web site management.

It should be noted that while CMS 66 may manage a content item, the content item may be stored at another location and a reference to the content item stored in repository 70. For example, a bank statement may reside in an enterprise system, but CMS 66 can access it.

In-context editing program 75 can provide a graphical user interface accessed by a keyboard and/or mouse and viewed on a computer monitor. According to one embodiment, in-context editing program 75 can be an Adobe Flash program, a Java program, a scripting language, or an AJAX (Asynchronous JavaScript and XML) application operating in a web browser, or a standalone program. Interface program 68 is a server program configured to interact with in-context editing program 75.

According to one embodiment, in-context editing program 75 can request information or initiate actions at server 24 by sending URL requests to server 24 that are translated into API calls to API 72 (e.g., by server program 48 or other program). Requests for data or to take actions can be sent as URL requests to server 24. Based on the URL, CMS 66 will return the appropriate data or take the appropriate actions.

Figure 2:
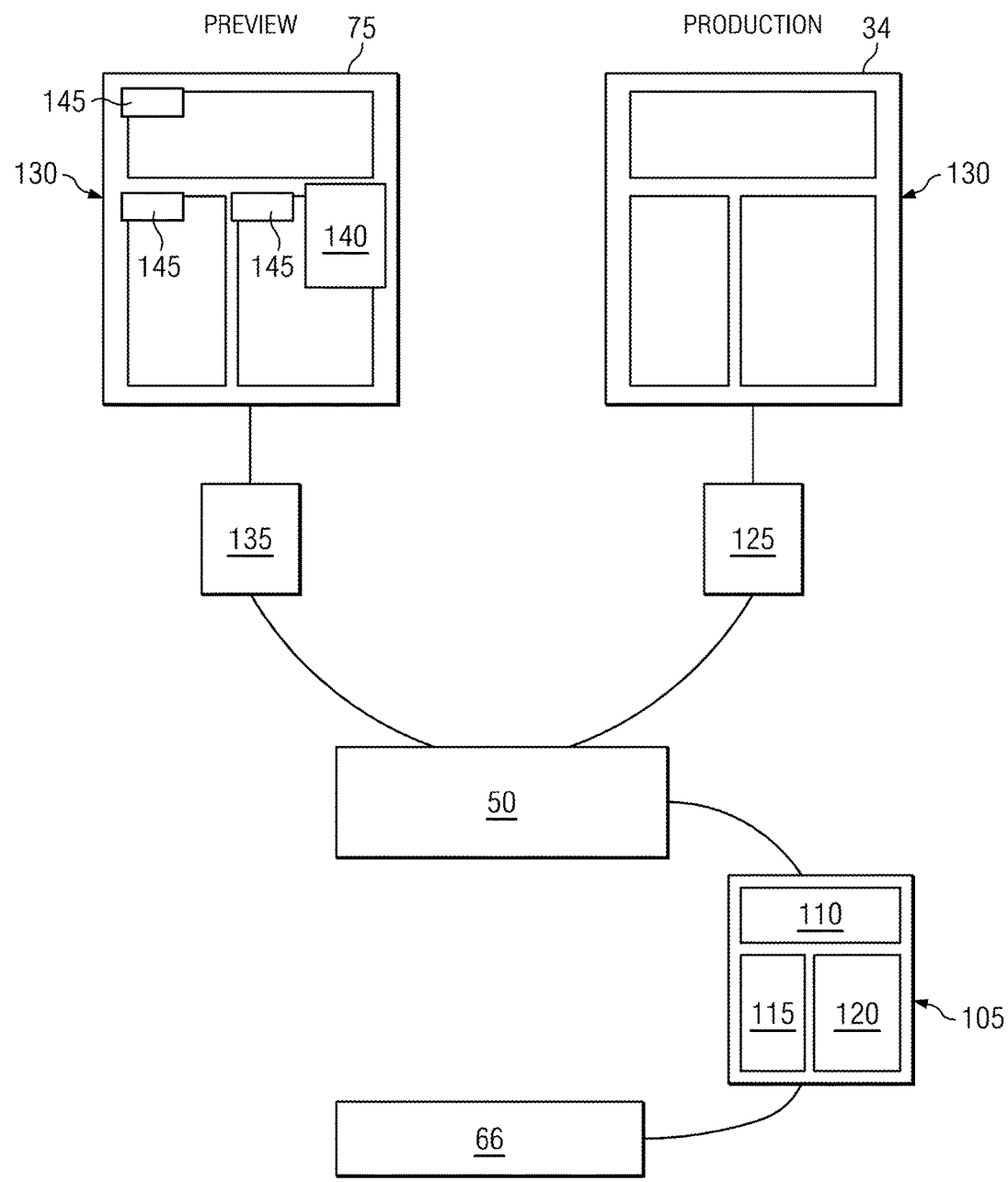
FIG. 2 is a diagram illustrating how a web page is provided to a user in a production environment and a preview environment in accordance with one embodiment.

FIG. 2 is a diagrammatic representation of one embodiment of providing a web page to a user in a production environment and a preview environment. In the production environment, a client 22 (FIG. 1) can request web pages using browser 34. In response to calls from server program 48 (FIG. 1), page generator program 50 can generate a file for a web page.

In general, page generator program 50 can request content for the web page from CMS 66 to build the web page. In one embodiment, the web page is laid out according to a template 105. Template 105 provides a pattern for the web page. A template defines regions (e.g., regions 110, 115 and 120) that define where content appears in the page. Each region can be populated by one or more components including, but not limited navigation components, text components, content items, content lists, images, smart lists, or other information. Template 105 can also specify what actions are available for a component (e.g., change, move, remove or other action).

Based on template 105, page generator 50 can generate a web page file 125 to send to browser 34 to cause browser 34 to render a production view 130 of the web page. This may include causing the browser to execute scripts, make additional requests or take other actions used to render web pages.

In a preview environment, in-context editing program 75 interfaces with CMS 66 to edit items in the web page. When a web page is accessed by in-context editing program 75, page generator 50 can build a web page file 135 that will cause in-context editing program to render the production view 130 of the web page with an overlay of editing tools. According to one embodiment, the tools can be overlaid as a "div" overlay through CSS.

Page generator 50, can parse the template to determine the regions where components are placed. For each region and/or component in a region, the types of actions that are available can be determined. This can be based on metadata associated with the template, metadata associated with the components or other information. Page generator 50 can change the DOM and HTML of the web page to include information for the editing tools in web page file 135.

According to one embodiment, a JavaScript library is provided to parse the template and attach the corresponding editing tools to each component or region. The tools themselves can be rendered and positioned using World Wide Web Consortium (W3C) standards such as CSS and JavaScript. Because the tools are rendered in the browser environment of in-context editing program 75, they can be easily enabled or disabled without needing a full page refresh.

According to one embodiment, editing tools can include a set of editing tools to allow editing of the overall page or template, shown as the floating tools palette 140. Additionally, editing tools applicable to individual components can be displayed near the associated region or component (shown as component menus 145 at the top corner of each region). Editable components or regions can be demarcated. For example, editable regions can be outlined with a dashed line or other indicator. The various editing tools are overlaid on view 130 so that they do not distort the production view.

Figure 3:
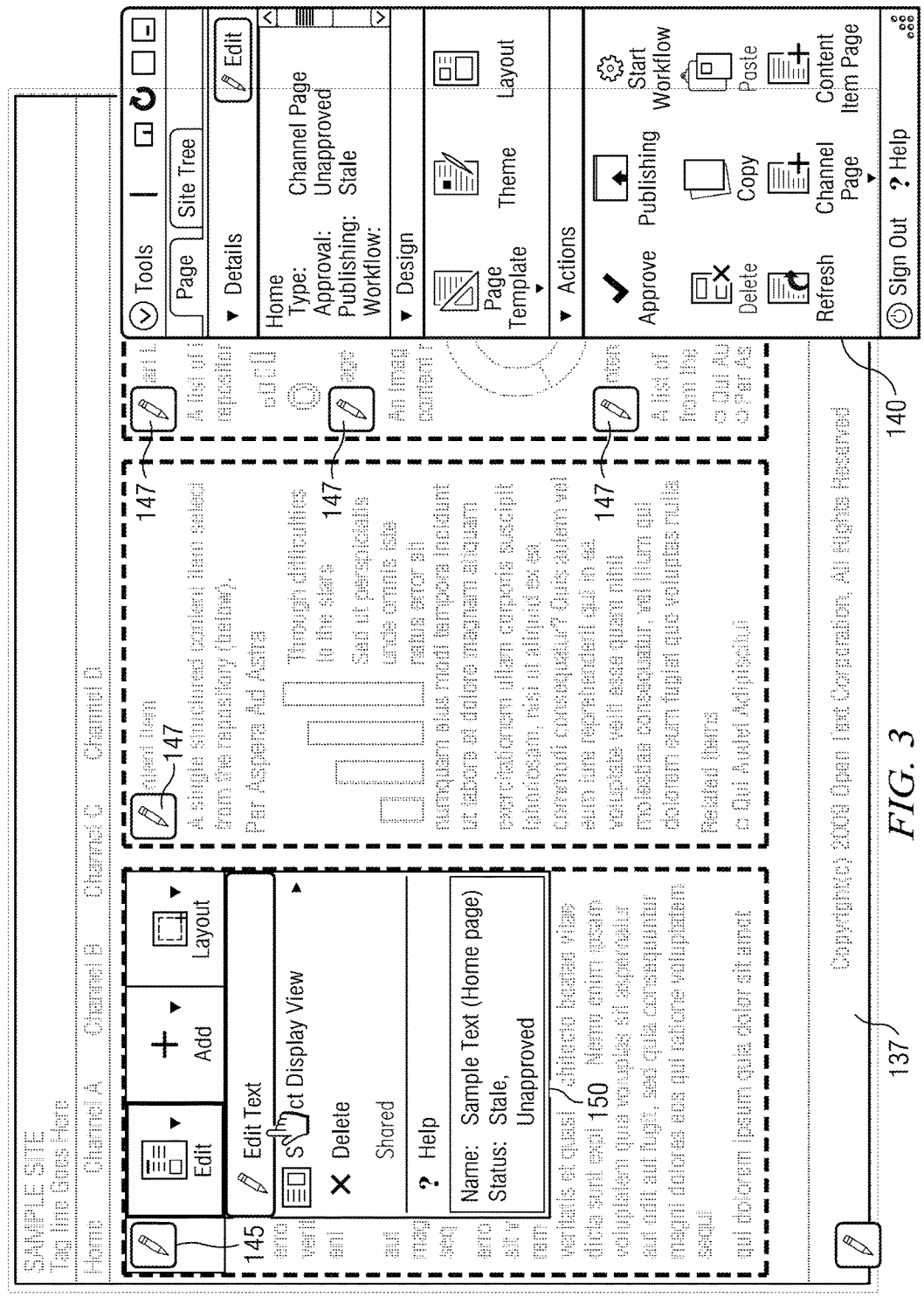
FIG. 3 is a diagram illustrating the presentation of tools to a user for in-context editing in accordance with one embodiment.

FIG. 3 is a diagrammatic representation of one embodiment of presenting tools to a user for in-context editing. An editable web page image 137 is rendered in the web browser showing a production view of the web page (the web page as it would appear in the production environment). A tools palette 140 is presented floating over the production view of the web site. Each component of the web site is presented with a component menu icon 147. When the user clicks on the component menu icon 147, the user is presented with a component menu with icons representing various types of actions the user can take with respect to the component. When the user scrolls over each icon, a drop down menu 150 of actions appears.

The actions made available for a page or component of the page can be based on settings in template 105 (FIG. 2), the type of component, user permissions or other information. For example, one set of options may be available for a text component while another set is available for an image component. As another example, one type of administrator may have permissions to edit text components, but not image components, while another type of administrator may have permission to edit both types of components.

When a user edits a component, the region of the web page in which the component is positioned or the component itself is refreshed to show the changed web page in the GUI. This can be done without refreshing the remainder of the page. Because the edits take place not just in the production view, but in the preview environment, the user sees in near real time how the production view of the web page will look when the changes are implemented.

It may not be desirable for the changes to appear in the production environment until the changes have been approved or published. In one embodiment, edits are not pushed to the production environment until the occurrence of a predefined event. To maintain separation between the production environment and preview environment, the in-context editing environment functions as an overlay of the underlying production web site. The page generator can use unique namespaces for JavaScript, CSS or HTML elements used in the preview environment. The DOM/HTML changes used to provide in-context editing are inserted using unique namespaced ids that will not conflict with the production environment or vice versa. Similarly, CSS used for the preview environment uses unique namespacing to avoid affecting the production environment. The in-context editing JavaScript also uses namespacing to avoid polluting the production environment. The JavaScript namespacing can be further extended to third party libraries which can be re-namespaced for the preview environment. This allows a web site provider to use the same third party library but with a different version and/or different plugins & extensions in the production environment without being affected by the in-context editing environment.

Thus, embodiments described herein provide a system for in-context editing that overlays editing/workflow tools on a production view of web page. Tools can be presented in a variety of formats. For example, tool icons can be presented in floating tool palettes. In other embodiments, tool icons can be presented proximate to or on the region or component to which the tools apply. Editing and workflow actions can be made available by clicking on the icons or from drop-down lists accessible from the icons. The in-context editing environment can limit the actions available to a user based on information specified in a page template, metadata associated with a component of the web page, user permissions or other information.

Edits and actions taken during in-context editing can be done in a unique namespace and the changes to the web page pushed to the production namespace at the occurrence of a specified event (e.g., publication). Consequently, editing will not change the production environment until the appropriate time in a workflow.

Embodiments described herein can be implemented in a computing environment having one or more client machines connected to one or more servers by a network. The network can be characterized as an internal network and/or external network. The Internet might be an example of an external network and a company's intranet might be an example of an internal network. Each network can be bi-directionally coupled to a variety of networked systems, devices, repositories, etc.

Virtually any piece of hardware or electronic device capable of running appropriate software may be a server or client. As an example, a computer may include a central processing unit (CPU), read-only memory (ROM), random access memory (RAM), hard drive or non-volatile memory, and input/output (I/O) device(s). An I/O device may be a keyboard, monitor, printer, electronic pointing device (e.g., mouse, trackball, etc.), or the like. The hardware configuration of the computer can be representative to other devices and computers alike coupled to the network (e.g., desktop computers, laptop computers, personal digital assistants, handheld computers, cellular phones, and any electronic devices capable of storing and processing information and network communication.

Embodiments disclosed herein may be implemented in suitable software including computer-executable instructions. As one skilled in the art can appreciate, a computer program product implementing an embodiment disclosed herein may comprise one or more non-transitory computer readable storage media storing computer instructions translatable by one or more processors in a computing environment. Examples of computer readable media may include, but are not limited to, volatile and non-volatile computer memories and storage devices such as ROM, RAM, HD, direct access storage device arrays, magnetic tapes, floppy diskettes, optical storage devices, etc. In an illustrative embodiment, some or all of the software components may reside on a single server computer or on any combination of separate server computers.

Although the foregoing specification describes specific embodiments, numerous changes in the details of the embodiments disclosed herein and additional embodiments will be apparent to, and may be made by, persons of ordinary skill in the art having reference to this description. In this context, the specification and figures are to be regarded in an illustrative rather than a restrictive sense, and all such modifications are intended to be included within the scope of this disclosure. Accordingly, the scope of the present disclosure should be determined by the following claims and their legal equivalents.

Although the foregoing specification describes specific embodiments, numerous changes in the details of the embodiments disclosed herein and additional embodiments will be apparent to, and may be made by, persons of ordinary skill in the art having reference to this description. In this context, the specification and figures are to be regarded in an illustrative rather than a restrictive sense, and all such modifications are intended to be included within the scope of this disclosure.

Those of skill will appreciate that the various illustrative logical blocks, modules, circuits, and algorithm steps described in connection with the embodiments disclosed herein may be implemented as electronic hardware, computer software (including firmware,) or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Those of skill in the art may implement the described functionality in varying ways for each particular application, but such implementation decisions should not be interpreted as causing a departure from the scope of the present disclosure.

The various illustrative logical blocks, modules, and circuits described in connection with the embodiments disclosed herein may be implemented or performed with application specific integrated circuits (ASICs), field programmable gate arrays (FPGAs), general purpose processors, digital signal processors (DSPs) or other logic devices, discrete gates or transistor logic, discrete hardware components, or any combination thereof designed to perform the functions described herein. A computer or general purpose processor may be any conventional processor, controller, microcontroller, state machine or the like. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in software (program instructions) executed by a processor, or in a combination of the two. The steps of the methods or algorithms herein are intended to be exemplary, and alternative embodiments may combine steps, split a single step into multiple steps, perform the steps in a different order, or have similar variations form the foregoing embodiments.

The benefits and advantages which may be provided have been described above with regard to specific embodiments. These benefits and advantages, and any elements or limitations that may cause them to occur or to become more pronounced are not to be construed as critical, required, or essential features of any or all of the claims. As used herein, the terms "comprises," "comprising," or any other variations thereof, are intended to be interpreted as non-exclusively including the elements or limitations which follow those terms. Accordingly, a system, method, or other embodiment that comprises a set of elements is not limited to only those elements, and may include other elements not expressly listed or inherent to the claimed embodiment.

While particular embodiments have been described, it should be understood that the embodiments are illustrative and that the scope of the claims are not limited to these embodiments. Many variations, modifications, additions and improvements to the embodiments described above are possible. It is contemplated that these variations, modifications, additions and improvements fall within the scope of the invention as detailed within the following claims.

What is claimed is:

1. A system for facilitating in-context editing of web pages in a client browser at a client device, the system comprising:
   a network interface to connect to a client device over a network;
   a processor;
   a non-transitory computer readable medium storing a set of computer instructions executable by the processor to:
      receive from the client device, via the network, a request for a web page;
      determine an in-context editing tool associated with a first component of the web page based on a template associated with the web page, wherein the template specifies settings associated with the first component of the web page;
      generate a production view of the web page and generate an overlay of including the in-context editing tool based on the determined in-context editing tool;
      transmit page source to the client device corresponding to the production view and the overlay of the in-context editing tool, the page source configured to cause the client browser to operate alternatively in a plurality of modes and to switch between a first mode and a second mode without refreshing the web page, wherein:
         in the first mode of the plurality of modes, the in-context editing tool is enabled and the client browser renders the overlay of the in-context editing tool superimposed on the production view of the web page with the in-context editing tool applicable to the first component of the web page displayed near the first component without distorting a size and placement of components of the production view; and
         in the second mode of the plurality of modes, the in-context editing tool is disabled and the client browser renders the production view of the web page but hides the overlay of the in-context editing tool; and
      receive an edit to the first component in the production view using the in-context editing tool and refresh the first component without refreshing the entire web page.

2. The system of claim 1, wherein the first component is in a first namespace and the in-context editing tool comprises an element in a second namespace such that the client browser switches between the first mode and the second mode by disabling the second namespace.

3. The system of claim 2, wherein the first namespace is a production environment namespace and the second namespace is a preview environment namespace.

4. The system of claim 2, wherein the edited first component is maintained in the second namespace until an occurrence of an event and, at the occurrence of the event, the edited first component is transferred to the first namespace.

5. The system of claim 2, wherein switching between the first mode and second comprises enabling or disabling all template elements included in the second namespace associated with the in-context editing tools.

6. The system of claim 2, wherein the in-context editing tool includes a Javascript, CSS or HTML element.

7. The system of claim 6, wherein the in-context editing tool is provided in association with the DOM or HTML of the page source.

8. A method for facilitating in-context editing of web pages in a client browser at a client device, the method comprising:
    receiving from a client device, via a network, a request for a web page;
    determining an in-context editing tool associated with a first component of the web page based on a template associated with the web page, wherein the template specifies settings associated with the first component of the web page;
    generating a production view of the web page and generate an overlay of including the in-context editing tool based on the determined in-context editing tool;
    transmitting page source to the client device corresponding to the production view and the overlay of the in-context editing tool, the page source configured to cause the client browser to operate alternatively in a plurality of modes and to switch between a first mode and a second mode without refreshing the web page, wherein:
        in the first mode of the plurality of modes, the in-context editing tool is enabled and the client browser renders the overlay of the in-context editing tool superimposed on the production view of the web page with the in-context editing tool applicable to the first component of the web page displayed near the first component without distorting a size and placement of components of the production view; and
        in the second mode of the plurality of modes, the in-context editing tool is disabled and the client browser renders the production view of the web page but hides the overlay of the in-context editing tool; and
    receiving an edit to the first component in the production view using the in-context editing tool and refresh the first component without refreshing the entire web page.

9. The method of claim 8, wherein the first component is in a first namespace and the in-context editing tool comprises an element in a second namespace such that the client browser switches between the first mode and the second mode by disabling the second namespace.

10. The method of claim 9, wherein the first namespace is a production environment namespace and the second namespace is a preview environment namespace.

11. The method claim 9, wherein the edited first component is maintained in the second namespace until an occurrence of an event and, at the occurrence of the event, the edited first component is transferred to the first namespace.

12. The method of claim 9, wherein switching between the first mode and second comprises enabling or disabling all template elements included in the second namespace associated with the in-context editing tools.

13. The method of claim 9, wherein the in-context editing tool includes a Javascript, CSS or HTML element.

14. The method of claim 13, wherein the in-context editing tool is provided in association with the DOM or HTML of the page source.

15. A non-transitory computer readable medium comprising instructions for facilitating in-context editing of web pages in a client browser at a client device, the instructions executable for:
    receiving from a client device, via a network, a request for a web page;
    determining an in-context editing tool associated with a first component of the web page based on a template associated with the web page, wherein the template specifies settings associated with the first component of the web page;
    generating a production view of the web page and generate an overlay of including the in-context editing tool based on the determined in-context editing tool;
    transmitting page source to the client device corresponding to the production view and the overlay of the in-context editing tool, the page source configured to cause the client browser to operate alternatively in a plurality of modes and to switch between a first mode and a second mode without refreshing the web page, wherein:
        in the first mode of the plurality of modes, the in-context editing tool is enabled and the client browser renders the overlay of the in-context editing tool superimposed on the production view of the web page with the in-context editing tool applicable to the first component of the web page displayed near the first component without distorting a size and placement of components of the production view; and
        in the second mode of the plurality of modes, the in-context editing tool is disabled and the client browser renders the production view of the web page but hides the overlay of the in-context editing tool; and
    receiving an edit to the first component in the production view using the in-context editing tool and refresh the first component without refreshing the entire web page.

16. The non-transitory computer readable medium of claim 15, wherein the first component is in a first namespace and the in-context editing tool comprises an element in a second namespace such that the client browser switches between the first mode and the second mode by disabling the second namespace.

17. The non-transitory computer readable medium of claim 16, wherein the first namespace is a production environment namespace and the second namespace is a preview environment namespace.

18. The non-transitory computer readable medium of claim 16, wherein the edited first component is maintained in the second namespace until an occurrence of an event and, at the occurrence of the event, the edited first component is transferred to the first namespace.

19. The non-transitory computer readable medium of claim 16, wherein switching between the first mode and second comprises enabling or disabling all template elements included in the second namespace associated with the in-context editing tools.

20. The non-transitory computer readable medium of claim 16, wherein the in-context editing tool includes a Javascript, CSS or HTML element.

21. The non-transitory computer readable medium of claim 20, wherein the in-context editing tool is provided in association with the DOM or HTML of the page source.

* * * * *